United States Patent
Chen et al.

(10) Patent No.: US 9,872,878 B2
(45) Date of Patent: Jan. 23, 2018

(54) ATRACTYLODES LANCEA EXTRACT FEED ADDITIVE AND PREPARATION METHOD THEREOF

(71) Applicant: Shanghai Zhao Xiang Biological Technology Co., LTD, Shanghai (CN)

(72) Inventors: Jiaming Chen, Shanghai (CN); Shunjie Huang, Shanghai (CN); Xuefeng Chen, Shanghai (CN); Zili Chen, Shanghai (CN); Ziqiang Chen, Shanghai (CN); Ting Shu, Shanghai (CN)

(73) Assignee: Shanghai Zhao Xiang Biological Technology Co., LTD, Shanghai (CN)

(*) Notice: Subject to any disclaimer, the term of this patent is extended or adjusted under 35 U.S.C. 154(b) by 287 days.

(21) Appl. No.: 14/687,906

(22) Filed: Apr. 15, 2015

(65) Prior Publication Data
US 2015/0297656 A1    Oct. 22, 2015

(30) Foreign Application Priority Data

Apr. 16, 2014    (CN) .......................... 2014 1 0152949

(51) Int. Cl.
| | | |
|---|---|---|
| *A61K 36/284* | (2006.01) | |
| *A23K 40/00* | (2016.01) | |
| *A23K 10/30* | (2016.01) | |
| *A23K 20/163* | (2016.01) | |
| *A23K 20/10* | (2016.01) | |
| *A23K 20/28* | (2016.01) | |
| *A23K 50/30* | (2016.01) | |

(52) U.S. Cl.
CPC ............ *A61K 36/284* (2013.01); *A23K 10/30* (2016.05); *A23K 20/10* (2016.05); *A23K 20/163* (2016.05); *A23K 20/28* (2016.05); *A23K 40/00* (2016.05); *A23K 50/30* (2016.05); *A61K 2236/00* (2013.01)

(58) Field of Classification Search
None
See application file for complete search history.

(56) References Cited

U.S. PATENT DOCUMENTS

| | | | | |
|---|---|---|---|---|
| 6,068,845 A | * | 5/2000 | Aoki ................... | A61K 8/4926 424/407 |
| 2008/0095870 A1 | * | 4/2008 | Chao ................... | A61K 36/284 424/769 |

* cited by examiner

*Primary Examiner* — Susan Hoffman

(57) ABSTRACT

An *Atractylodes Lancea* extract feed additive and a preparation method thereof are provided. The *Atractylodes Lancea* extract feed additive takes an *Atractylodes Lancea* extract and a carrier as raw materials. The *Atractylodes Lancea* extract is prepared by the ultrasonic auxiliary water extraction. The preparation method of the present invention has less raw material waste, high activity component content in the extract and acquisition rate of the extractum, which facilitates improving the effect efficiency and reducing production cost. The *Atractylodes Lancea* extract feed additive as a natural plant feed additive is capable of reducing malaria incidence, restoring consciousness and relieving uneasiness, and diuretically swelling.

19 Claims, No Drawings

ATRACTYLODES LANCEA EXTRACT FEED ADDITIVE AND PREPARATION METHOD THEREOF

CROSS REFERENCE OF RELATED APPLICATION

The present invention claims priority under 35 U.S.C. 119(a-d) to CN 201410152949.3, filed Apr. 16, 2014.

BACKGROUND OF THE PRESENT INVENTION

Field of Invention

The present invention relates to a Chinese herbal medicine feed field, and more particularly to an *Atractylodes Lancea* extract feed additive and a preparation method thereof.

Description of Related Arts

Modern aquaculture has large feeding density. Environment stresses have serious effects on growth performance of pigs, and especially high temperature and high humidity are the most common and serious environment stress. Pigs are homeothermal animals, because adult pigs have undeveloped subcutaneous fat thick sweat gland and their living environment disadvantages are easy to be amplified, malaria is easy to occur to pigs. Furthermore, pigs have slower body heat dissipation, so they are very heat-intolerant. Continuous high temperature in summer results in heat stress, by changing physiological and biochemical responses of pigs, the feed intake, the daily gain and the feed rate of pigs are reduced for changing blood biochemical indexes of stock boars, so that the sexual desire of stock boars is reduced, the semen quality is decreased, the normal endocrine function of pregnant sows is interfered, the uterine endocrine and the hormone excretion thereof are disordered, the embryo survival is decreased, thereby reducing production performances and economic benefits of the pig industry. Therefore, it is very important to develop a highly effective, safe, green and environment-friendly anti-heat stress feed additive special for pigs.

Plant extract is one of main feed antibiotic substitutes and is a natural substance. It is capable of promoting animal growth, improving animal constitution, increasing metabolism, improving production performance, resisting stress, preventing diseases, etc., which is in the leading level in China. Foreign countries have very strict requirements for food, and especially, European Union which is internationally the earliest, largest and most strictest region where feed antibiotic is strictly prohibited. Feed additives are successfully prohibited in European Union, the reason is that: besides excellent feeding and management supporting facilities, there is a very important physical measurement that feed antibiotic is replaced by the plant extract (Chinese herbal medicine). The Chinese herbal medicine plays a very important role in successfully prohibiting feed antibiotic.

*Atractylodes Lancea* has some functions of drying dampness and strengthening the spleen, eliminating rheumatism; mainly treats retention of dampness in the middle-heater, arthralgia wind-cold dampness, food swelling and pain in knee, flaccid weakness, and passeriiformes night blindness, whose functions can be found from "Pearl Sac" and "Compendium of Materia Medica". It is a commonly seen Chinese medicine. Long-term application practices show that *Atractylodes Lancea* is safe and effective, and has great development value and research significances. It has not been reported that the value and effectiveness of *Atractylodes Lancea* used as feed.

SUMMARY OF THE PRESENT INVENTION

An object of the present invention is to overcome the shortcomings of the above prior art and provide an *Atractylodes Lancea* extract feed additive and a preparation method thereof. While extracting a traditional Chinese medicine plant, the most critical aspect is to select the solvent, set the steps, optimize the temperature and set ratios of components. It is found through a large number of experimental studies that the present invention achieves a most efficient, simple and practical method of preparing an *Atractylodes Lancea* extract without any pollutions, and extracts farthest active ingredients from the *Atractylodes Lancea* extract for preparing an *Atractylodes Lancea* extract feed additive to not only reduce malaria incidence, but also restore consciousness, relieve uneasiness, and diuretically swell of the livestock.

The above object is achieved by the technical solution as follows.

On the one hand, the present invention relates to an *Atractylodes Lancea* extract feed additive comprising an *Atractylodes Lancea* extract and a carrier, wherein the *Atractylodes Lancea* extract is prepared by an ultrasonic auxiliary water extraction.

Preferably, a weight ratio of the *Atractylodes Lancea* extract and the carrier is (1-2):(3-5).

Preferably, the carrier is a mixture of attapulgite and maltodextrin with a weight ratio of 1 (1-2).

On the other hand, the present invention also relates to a method of preparing the above *Atractylodes Lancea* extract feed additive, comprising steps of:

(1) pretreating and smashing *Atractylodes Lancea*, adding ethanol solution to immerse for 5-6 h; removing to an ultrasonic extractor for ultrasonically extracting at room temperature for 35-50 min; filtering after the extraction for obtaining a filtrate and a first solid residue; vacuum evaporating for removing ethanol in the filtrate to obtain a first extracting solution;

(2) adding eight times an amount of water into the first solid residue, boiling for 4-6 h at a steam pressure of 0.4-0.7 MPa, filtering to obtain a second extracting solution and a second solid residue;

(3) adding five times an amount of water into the second solid residue, boiling for 1-3 h at a steam pressure of 1.5-1.6 MPa, filtering to obtain a third extracting solution and a third solid residue;

(4) mixing the first extracting solution, the second extracting solution and the third extracting solution, concentrating for obtaining a first extractum; spraying and drying to obtain an *Atractylodes Lancea* extract dry powder; and (5) evenly mixing the *Atractylodes Lancea* extract dry powder with a carrier to obtain the *Atractylodes Lancea* extract feed additive.

Preferably, the step of pretreating and smashing *Atractylodes Lancea* comprises naturally drying and impurity removing stems and leafs of the *Atractylodes Lancea*, drying for 6 h at 60° C., smashing, and sieving through a sieve with an aperture of 1.2-1.5 mm. If a particle is undersize, the *Atractylodes Lancea* powder is easy to float on the feed liquid, so that the extraction effect is affected; if the particle is oversize, the extraction efficiency is reduced more.

Preferably, an amount of the added ethanol solution is 20-25 ml ethanol solution per gram *Atractylodes Lancea* powder, wherein a concentration of ethanol in the ethanol solution is 80 wt %-85 wt %. The concentration and amount of the ethanol solution have larger effects on the acquisition rate of the extractum. When the amount of the ethanol solution is increased to a certain degree (wherein a concentration of ethanol solution is 85 wt %, an amount thereof is that 25 ml ethanol solution is added per gram *Atractylodes Lancea*), increasing the amount of the ethanol solution has no obvious effects on the acquisition rate of the extractum. After overall consideration of cost and effect, 20-25 ml ethanol solution is added per gram *Atractylodes Lancea*, wherein when a concentration of ethanol in the ethanol solution is 80 wt %-85 wt %, the technology is best.

Preferably, while ultrasonically extracting, an ultrasonic frequency is 110-120 KHz.

Preferably, while ultrasonically extracting, moisture is distilled simultaneously for collecting a distillate. The distillate is *Atractylodes Lancea* volatile oil containing atractylol, atractylon and atractylodin, wherein atractylol is a mixture of β-eudesnol and hinesol with a ratio of 6:4. The atractylol is capable of promoting gastrointestinal motility and slightly contracting gastrointestinal smooth muscle. The atractylon and atractylodin are capable of resisting central nervous system, resisting hypoxia and organizing the stomach. According to the present invention, the distillate is sold as a secondary product and is capable of mixing with the first extraction solution, the second extraction solution and the third extraction solution, concentrating for subsequent preparation.

Preferably, in the step (2), acetic acid is added to adjust a PH value of solution to 6.5, and in the step (3), saturated NaOH is added to adjust a PH value of solution to 8.0.

Preferably, before spraying and drying, the step (4) further comprises steps of: eluting the first extractum with silica gel column chromatography gradient which takes petroleum ether/ethyl acetate as an eluent with a ratio of petroleum ether/ethyl acetate=5:1, 3:1 and 2:1, and an eluting time of 15 min, combining eluting solutions, concentrating for obtaining a second extractum, spraying and drying the second extractum to obtain the *Atractylodes Lancea* extract dry powder.

Compared with the prior art, the present invention has beneficial effects as follows.

(1) It is capable of reducing malaria incidence and relieving summer-heat.

(2) It is capable of preventing animal peptic ulcer and the occurrence of diarrhea.

(3) It has strong palatability, is capable of improving feed intake and promoting growing.

(4) It is natural and green without any chemical medicines or hormone.

These and other objectives, features, and advantages of the present invention will become apparent from the following detailed description, the accompanying drawings, and the appended claims.

DETAILED DESCRIPTION OF THE PREFERRED EMBODIMENT

The present invention is further explained in detail with the accompanying embodiments.

Example 1

The example 1 relates to an *Atractylodes Lancea* extract feed additive. A method of preparing the above *Atractylodes Lancea* extract feed additive comprises steps of:

Step 1: naturally drying and impurity removing stems and leafs of *Atractylodes Lancea*, drying for 6 h at 60° C., smashing, sieving through a sieve with an aperture of 1.2 mm, adding 20 ml, 85 wt % ethanol solution per gram *Atractylodes Lancea* to immerse for 6 h; removing to an ultrasonic extractor for ultrasonically extracting at room temperature and a frequency of 115 KHz for 45 min; filtering after the extraction for obtaining filtrate and a first solid residue; vacuum evaporating for removing ethanol in the filtrate to obtain a first extracting solution;

Step 2: adding eight times an amount of water into the first solid residue, boiling for 5 h at a steam pressure of 0.5 MPa, filtering to obtain a second extracting solution and a second solid residue;

Step 3: adding five times an amount of water into the second solid residue, boiling for 3 h at a steam pressure of 1.6 MPa, filtering to obtain a third extracting solution and a third solid residue;

Step 4: mixing the first extracting solution, the second extracting solution and the third extracting solution, concentrating till D (which is a proportion of the mixed solution)=0.6-1.2 for obtaining an extractum; putting the extractum into a spray dryer with an inlet air temperature of 180° C. and an outlet air temperature of 80° C. (which is able to be in a range of 70-90° C.) to obtain an *Atractylodes Lancea* extract dry powder; and Step 5: evenly mixing the *Atractylodes Lancea* extract dry powder with a carrier (which is a mixture of attapulgite and maltodextrin with a weight ratio of 1:1) to obtain the *Atractylodes Lancea* extract feed additive, wherein a weight ratio of the *Atractylodes Lancea* extract dry powder and the carrier is 1:3.

Comparative Example 1

The comparative example 1 relates to an *Atractylodes Lancea* extract feed additive. A method of preparing the above *Atractylodes Lancea* extract feed additive comprises steps of:

Step 1: naturally drying and impurity removing stems and leafs of *Atractylodes Lancea*, drying for 6 h at 60° C., smashing, sieving through a sieve with an aperture of 1.2 mm; adding the sieved *Atractylodes Lancea* into an alcohol extraction tank, adding eight times an amount of 85 wt % ethanol, boiling for 5 h at a steam pressure of 0.7 MPa, making an ethanol reflux; filtering after firstly extracting ethanol for obtaining a first filtrate and a first filter residue, wherein ethanol is recycled from the first filtrate by a decompression concentration tank till a concentration of the recycled ethanol is smaller than 60%, concentrating the first filtrate to obtain a concentrated solution;

Step 2: adding eight times an amount of 85 wt % ethanol into the first filter residue, boiling for 5 h at a steam pressure of 0.7 MPa, making an ethanol reflux, wherein ethanol is recycled till a concentration of the recycled ethanol is smaller than 60%, filtering to obtain a second filtrate and a second filter residue;

Step 3: adding five times an amount of water into the second filter residue, boiling for 3 h at a steam pressure of 1.4 MPa, filtering to obtain a third filtrate and a third filter residue; discarding the third filter residue;

Step 4: mixing the concentrated solution, the second filtrate and the third filtrate, concentrating till D (which is a proportion of the mixed solution)=0.6-1.2 for obtaining an extractum; putting the extractum into a spray dryer with an inlet air temperature of 180° C. and an outlet air temperature of 80° C. to obtain an *Atractylodes Lancea* extract dry powder; and Step 5: evenly mixing the *Atractylodes Lancea* extract dry powder with a carrier (which is a mixture of attapulgite and maltodextrin with a weight ratio of 1:1) to obtain the *Atractylodes Lancea* extract feed additive, wherein a weight ratio of the *Atractylodes Lancea* extract dry powder and the carrier is 1:3.

Example 2

An object of the example 2 is to study the effects of a PH value in a step of water extraction after ultrasonically extracting on a ratio of dry extraction and an extraction ratio of active components. The preparation method of the example 2 is as same as that of the example 1, and the differences therebetween are that: in the step (2) of the example 2, respectively add acetic acid to adjust a PH value of solution to 5.5, 6.0 and 6.5, and respectively add saturated NaOH to adjust a PH value of solution to 7.5, 8.0 and 9.0 in the step (3) of the example 2 for forming nine experimental groups, wherein nine experimental groups 2a-2i respectively correspond to nine groups of PH values in step (2) and step (3) which are respectively 5.5, 7.5; 5.5, 8.0; 5.5, 9.0; 6.0, 7.5; 6.0, 8.0; 6.0, 9.0; 6.5, 7.5; 6.5, 8.0; 6.5, 9.0.

Take 100 g *Atractylodes Lancea* medicinal material to make a comparative experiment on the example 1, the example 2 and the comparative example 1 as follows.

Measure the ratio of dry extraction: respectively mix the first extracting solution, the second extracting solution and the third extracting solution obtained by the above nine experimental groups and the example 1; the concentrated solution, the second filtrate and the third filtrate obtained by the comparative example 1, and concentrate the mixture to be with a volume of 500 ml, take 20 ml concentrated solution to a moisture analyzer for determining moisture, and calculate the ratio of dry extraction of the extract based on a moisture value.

Measurement results are shown in Table 1.

TABLE 1

| | EG 2a | EG 2b | EG 2c | EG 2d | EG 2e | EG 2f | EG 2g | EG 2h | EG 2i | E1 | CE1 |
|---|---|---|---|---|---|---|---|---|---|---|---|
| RODE (%) | 21.1 | 22.0 | 22.3 | 23.4 | 22.5 | 22.1 | 23.4 | 26.8 | 22.7 | 22.7 | 17.6 |

* Note:
Experimental Group is abbreviated as EG, Example 1 is abbreviated as E1, Comparative Example is abbreviated as CE1, and the ratio of dry extraction is abbreviated as RODE.

It can be seen from Table 1 that when acetic acid is added to adjust the PH value of solution to 6.5 in the step (2), and saturated NaOH is added to adjust the PH value of solution to 8.0 in the step (3), the ratio of dry extraction of the extract is best.

Example 3

The example 3 relates to an *Atractylodes Lancea* extract feed additive, the preparation method thereof is as same as that of the example 1 and the differences therebetween are as follows.

Before spraying drying, following steps further included: eluting the extractum with silica gel column chromatography gradient which takes petroleum ether/ethyl acetate as an eluent with a ratio of petroleum ether/ethyl acetate=10:1;

5:1; 3:1; 2:1; 1:1, 1:5 and an eluting time of 15 min, respectively collecting eluting solution, concentrating for obtaining a new extractum, spraying and drying to obtain the *Atractylodes Lancea* extract dry powder. Evenly mix the six groups of *Atractylodes Lancea* extract dry powder with a carrier (which is a mixture of attapulgite and maltodextrin with a weight ratio of 1:1) to obtain the *Atractylodes Lancea* extract feed additives which are respectively recorded as Experimental group 3a, Experimental group 3b, Experimental group 3c, Experimental group 3d, Experimental group 3e and Experimental group 3f, wherein a weight ratio of the *Atractylodes Lancea* extract dry powder and the carrier is 1:3.

Example 4

An object of the example 4 is to study the effects of various carriers on the *Atractylodes Lancea* extract feed additive. The preparation method thereof is as same as that of example 1 and the differences therebetween are as follows. The carriers are respectively selected from attapulgite, maltodextrin, maltodextrin and attapulgite with a weight ratio of 1:2, 2:1, 4:1, which are respectively recorded as Experimental group 4a, Experimental group 4b, Experimental group 4c, Experimental group 4d and Experimental group 4e.

Comparatively experiment on the examples 1, 3, 4 and the comparative example 1 at the experimental place of Yuanheng animal Chinese medicine research center, Shanghai of China. The experimental animals are three-breed growing-finishing pigs bred in the late and fed with mixing materials, wherein 650 g *Atractylodes Lancea* extract feed additives are added per ton fodder. No *Atractylodes Lancea* extract feed additive is added to the comparative group.

Experimental results are shown in Table 2.

TABLE 2

| Test indexes | | Daily gain (g) | Daily feed intake (g) | Feed conversion ratio | Rate of survival (%) | Malaria incidence (%) |
|---|---|---|---|---|---|---|
| Comparative Group | | 778 | 2382 | 22.01 | 96 | 26 |
| Comparative Example 1 | | 785 | 2380 | 5.52 | 97 | 19 |
| Example | 1 | 853 | 2288 | 2.58 | 100 | 12 |
| | 2h | 859 | 2285 | 2.35 | 100 | 11 |
| | 3a | 810 | 2335 | 2.59 | 98.5 | 14.7 |
| | 3b | 865 | 2278 | 2.05 | 100 | 9 |
| | 3c | 863 | 2275 | 2.12 | 100 | 8 |
| | 3d | 859 | 2270 | 2.08 | 100 | 8.5 |

TABLE 2-continued

| Test indexes | Daily gain (g) | Daily feed intake (g) | Feed conversion ratio | Rate of survival (%) | Malaria incidence (%) |
|---|---|---|---|---|---|
| 3e | 813 | 2345 | 2.53 | 98.9 | 13.2 |
| 3f | 819 | 2338 | 2.59 | 99 | 13.3 |
| 4a | 825 | 2365 | 2.90 | 97.5 | 16.5 |
| 4b | 836 | 2331 | 2.64 | 98.7 | 14.5 |
| 4c | 827 | 2345 | 2.89 | 98.5 | 15.8 |
| 4d | 855 | 2281 | 2.52 | 100 | 12 |
| 4e | 820 | 2352 | 3.02 | 98.5 | 16.5 |

It can be seen from Table 2 by comparing the examples 1, 4a, 4b, 4c, 4d and 4e that: the mixture of attapulgite and maltodextrin with a weight ratio of 1:(1-2) as the carrier is capable of playing a synergic role in the *Atractylodes Lancea* extract and reducing the malaria incidence of pigs. It can be found by comparing experimental groups in the example 3 that: when the eluent with the ratio of petroleum ether/ethyl acetate=5:1; 3:1; 2:1 is used, the eluted component is capable of significantly reducing the malaria incidence of pigs and improving rate of survival. All in all, the *Atractylodes Lancea* extract feed additive of the present invention is capable of preferably enhancing the animal immune function, resisting diseases, promoting growth, reducing the malaria incidence of pigs and improving rate of survival.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An *Atractylodes Lancea* extract feed additive, comprising an *Atractylodes Lancea* extract and a carrier, wherein the *Atractylodes Lancea* extract is prepared by a method comprising steps of:
    (1) pretreating and smashing *Atractylodes Lancea*, immersing the *Atractylodes Lancea* for 5-6 h after adding ethanol solution, and then ultrasonically extracting at room temperature for 35-50 min through an ultrasonic extractor, and then filtering, and obtaining a filtrate and a first solid residue; and then vacuum evaporating for removing ethanol in the filtrate, and finally obtaining a first extracting solution;
    (2) adding eight times an amount of water into the first solid residue, boiling for 4-6 h at a steam pressure of 0.4-0.7 MPa, filtering, and obtaining a second extracting solution and a second solid residue;
    (3) adding five times an amount of water into the second solid residue, boiling for 1-3 h at a steam pressure of 1.5-1.6 MPa, filtering, and obtaining a third extracting solution and a third solid residue; and
    (4) mixing the first extracting solution, the second extracting solution and the third extracting solution, and then concentrating and obtaining a first extractum; spraying and drying, and finally obtaining the *Atractylodes Lancea* extract.

2. The *Atractylodes Lancea* extract feed additive, as recited in claim 1, wherein a weight ratio of the *Atractylodes Lancea* extract and the carrier is 1:3, and the carrier is a mixture of attapulgite and maltodextrin with a weight ratio of 1:(1-2).

3. A method of preparing an *Atractylodes Lancea* extract feed additive, comprising steps of:
    (1) pretreating and smashing *Atractylodes Lancea*, immersing the *Atractylodes Lancea* for 5-6 h after adding ethanol solution, and then ultrasonically extracting at room temperature for 35-50 min through an ultrasonic extractor, and then filtering, and obtaining a filtrate and a first solid residue; and then vacuum evaporating for removing ethanol in the filtrate, and finally obtaining a first extracting solution;
    (2) adding eight times an amount of water into the first solid residue, boiling for 4-6 h at a steam pressure of 0.4-0.7 MPa, filtering to obtain a second extracting solution and a second solid residue;
    (3) adding five times an amount of water into the second solid residue, boiling for 1-3 h at a steam pressure of 1.5-1.6 MPa, filtering to obtain a third extracting solution and a third solid residue;
    (4) mixing the first extracting solution, the second extracting solution and the third extracting solution, concentrating for obtaining a first extractum; spraying and drying to obtain an *Atractylodes Lancea* extract dry powder; and
    (5) evenly mixing the *Atractylodes Lancea* extract dry powder with a carrier to obtain the *Atractylodes Lancea* extract feed additive.

4. The method, as recited in claim 3, wherein the step of pretreating and smashing *Atractylodes Lancea* comprises naturally drying and removing stems and leafs of the *Atractylodes Lancea*, drying for 6 h at 60° C., smashing, and sieving through a sieve with an aperture of 1.2-1.5 mm.

5. The method, as recited in claim 3, wherein an amount of the added ethanol solution is 20-25 ml ethanol solution per gram *Atractylodes Lancea*, wherein a concentration of ethanol in the ethanol solution is 80 wt %-85 wt %.

6. The method, as recited in claim 4, wherein an amount of the added ethanol solution is 20-25 ml ethanol solution per gram *Atractylodes Lancea*, wherein a concentration of ethanol in the ethanol solution is 80 wt %-85 wt %.

7. The method, as recited in claim 3, wherein while ultrasonically extracting, an ultrasonic frequency is 110-120 KHz.

8. The method, as recited in claim 6, wherein while ultrasonically extracting, an ultrasonic frequency is 110-120 KHz.

9. The method, as recited in claim 4, wherein while ultrasonically extracting, moisture is distilled simultaneously for collecting a distillate.

10. The method, as recited in claim 8, wherein while ultrasonically extracting, moisture is distilled simultaneously for collecting a distillate.

11. The method, as recited in claim 4, wherein in the step (2), acetic acid is added to adjust a PH value of solution to 6.5, and in the step (3), saturated NaOH is added to adjust a PH value of solution to 8.0.

12. The method, as recited in claim 10, wherein in the step (2), acetic acid is added to adjust a PH value of solution to 6.5, and in the step (3), saturated NaOH is added to adjust a PH value of solution to 8.0.

13. The method, as recited in claim 4, wherein before spraying and drying, the step (4) further comprising steps of: eluting the first extractum with silica gel column chromatography gradient which takes petroleum ether/ethyl acetate as an eluent and eluting with petroleum ether/ethyl acetate at a ratio of 5:1, 3:1 and 2:1, and an eluting time of 15 min, combining eluting solutions, concentrating for obtaining a second extractum, spraying and drying the second extractum to obtain the *Atractylodes Lancea* extract dry powder.

14. The method, as recited in claim 12, wherein before spraying and drying, the step (4) further comprising steps of: eluting the first extractum with silica gel column chromatography gradient which takes petroleum ether/ethyl acetate as an eluent and eluting with petroleum ether/ethyl acetate at a ratio of 5:1, 3:1 and 2:1, and an eluting time of 15 min, combining eluting solutions, concentrating for obtaining a second extractum, spraying and drying the second extractum to obtain the *Atractylodes Lancea* extract dry powder.

15. The method, as recited in claim 3, wherein a weight ratio of the *Atractylodes Lancea* extract dry power and the carrier is (1-2):(3-5).

16. The method, as recited in claim 13, wherein a weight ratio of the *Atractylodes Lancea* extract dry power and the carrier is (1-2):(3-5).

17. The method, as recited in claim 14, wherein a weight ratio of the *Atractylodes Lancea* extract dry power and the carrier is (1-2):(3-5).

18. The method, as recited in claim 4, wherein the carrier is a mixture of attapulgite and maltodextrin with a weight ratio of 1:(1-2).

19. The method, as recited in claim 17, wherein the carrier is a mixture of attapulgite and maltodextrin with a weight ratio of 1:(1-2).

* * * * *